Figure 1:
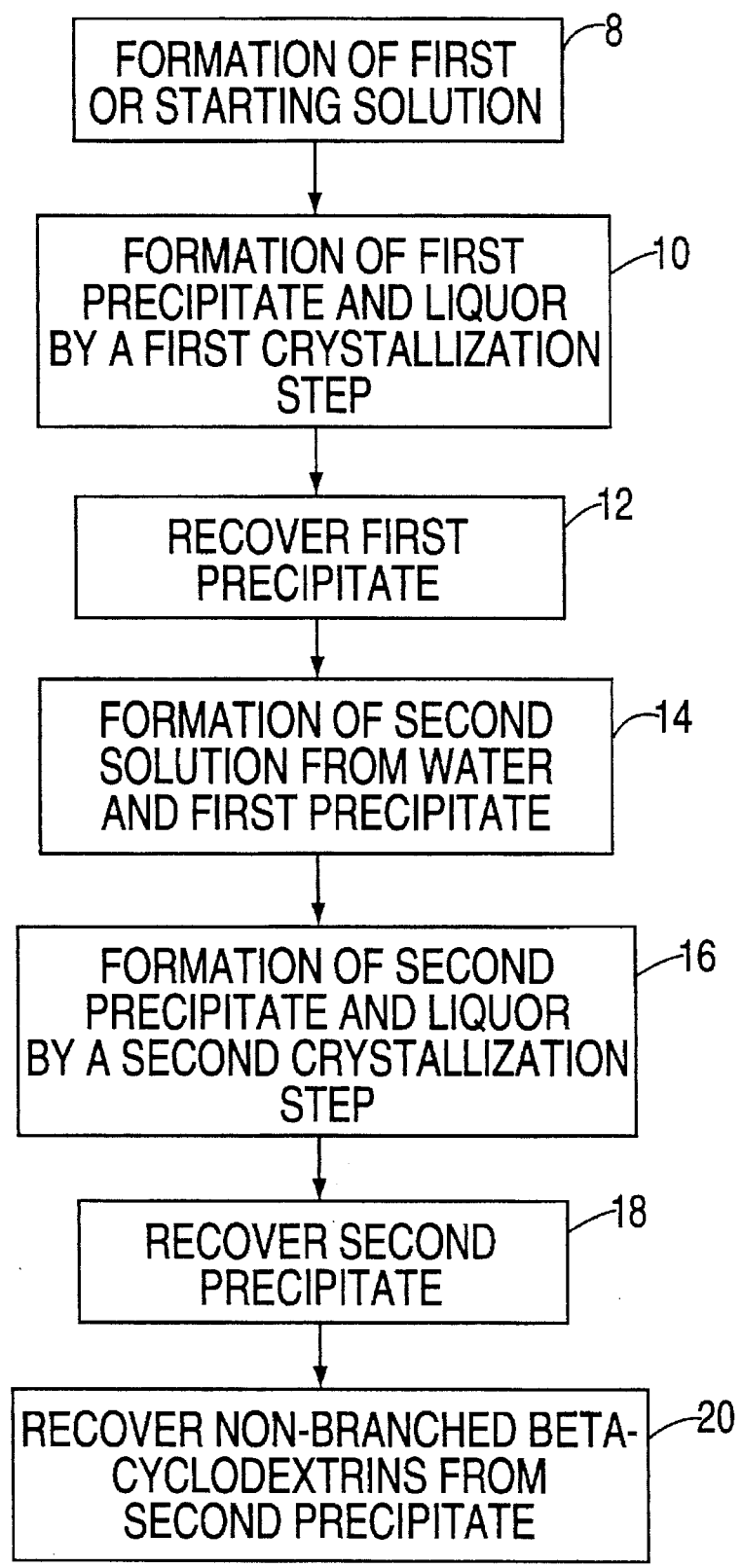

United States Patent [19]

Shieh et al.

[11] Patent Number: 5,658,390
[45] Date of Patent: Aug. 19, 1997

[54] PURIFICATION OF BETA CYCLODEXTRIN

[75] Inventors: Wen Shieh; Allan Hedges, both of Crown Point, Ind.

[73] Assignee: American Maize-Products Company, Hammond, Ind.

[21] Appl. No.: 268,196

[22] Filed: Jun. 29, 1994

[51] Int. Cl.$^6$ ............... C08B 30/00; C13J 1/06; C13D 3/16; C07H 1/00
[52] U.S. Cl. ............... 127/34; 127/40; 127/46.1; 127/55; 127/58; 127/61; 536/1.11; 536/103; 536/124; 536/127
[58] Field of Search ............... 127/34, 40, 46.1, 127/55, 58, 61; 536/1.11, 103, 124, 127

[56] References Cited

U.S. PATENT DOCUMENTS

| | | | |
|---|---|---|---|
| 3,086,009 | 4/1963 | Zuschek et al. | 260/233.3 |
| 3,425,910 | 2/1969 | Armbruster et al. | 195/31 |
| 4,384,898 | 5/1983 | Okada et al. | 127/40 |
| 4,555,504 | 11/1985 | Jones | 514/26 |
| 4,808,232 | 2/1989 | Beesley | 127/46.1 |
| 4,840,679 | 6/1989 | Ammeraal et al. | 127/40 |
| 4,904,306 | 2/1990 | Ammeraal | 127/46.1 |
| 4,970,164 | 11/1990 | Yang et al. | 435/280 |
| 5,007,967 | 4/1991 | Ammeraal | 127/46.1 |
| 5,229,370 | 7/1993 | Ammeraal | 514/26 |

FOREIGN PATENT DOCUMENTS 2206583 of 0000 United Kingdom ............ C08B 37/16

OTHER PUBLICATIONS

Jozsef Szejtli: "Cyclodextrin Technology" 1988, Kluwer Academic Publishers, Dordrecht XP000125912 Month N/A.

*Primary Examiner*—Glenn A. Caldarola
*Assistant Examiner*—Patricia L. Hailey
*Attorney, Agent, or Firm*—Bierman, Muserlian and Lucas

[57] ABSTRACT

A method for purifying non-branched beta cyclodextrin from aqueous solutions is disclosed. The process entails a plurality of independent crystallization steps.

7 Claims, 2 Drawing Sheets

PURIFICATION OF BETA CYCLODEXTRIN

This invention relates to a process for purifying beta cyclodextrin and, more specifically, to a process for removing branched beta cyclodextrin from an aqueous solution containing both branched and non-branched beta cyclodextrin by means of a plurality of crystallization steps.

Cyclodextrins, also called Schardingers dextrins, cycloamyloses, cyclomaltoses and cycloglucans, are cyclic oligomers of anhydroglucose, bonded together by alpha 1,4 bonds. If the cyclic oligosaccharide has six monomers, it is called alpha cyclodextrin; if seven, beta cyclodextrin; and if eight, gamma cyclodextrin. These six-, seven- and eight-membered rings are also referred to as cyclomaltohexaose, cyclomaltoheptaose and cyclomaltooctaose, respectively.

Branched cyclodextrins were described as early as 1965 by French and his co-workers (see French et al., Archives of Biochem. and Biophys. Volume III, pages 153–160, 1965) but have been studied very little until recently. Branched cyclodextrins comprise the cyclic structure of alpha 1,4 bonded anhydroglucose off of which one or more anhydroglucose monomers are bonded by alpha 1,6 bonds. The branch itself can comprise more than one anhydroglucose monomer such that the branch is an oligomer or polymer. These additional anhydroglucose monomers which make up the branched structure are bonded together by alpha 1,4 bonds. Branched beta cyclodextrin is relatively soluble in water compared to non-branched beta cyclodextrin. Specifically, non-branched beta cyclodextrin has a solubility of about 2% by weight, while branched beta cyclodextrin has a solubility of about 50% by weight and above.

For the purposes of definition, the term "beta cyclodextrin" without the modifying word "branched" or "non-branched" means both branched beta cyclodextrin and non-branched beta cyclodextrin. Branched and nonbranched beta cyclodextrins will be specifically identified as such.

Beta cyclodextrins are produced by treating a starch slurry with an enzyme, cyclodextrin glycosyltransferase (CGT) at the appropriate pH, temperature and time for the selected CGT. The starch may be from any selected plant variety. The enzyme CGT is obtained from microorganisms such as *Bacillus macerans, B. megaterium, B. circulans, B. stearothermophilus* and Bacillus sp. (alkalophilic) as well as others. The parameters for the reaction between the selected CGT enzyme and the selected starch are conventional and well described in the literature. Conventionally, the starch is slurried in aqueous solution at a concentration up to about 35% by weight solids. The slurry is then subjected to gelatinization and liquefaction by enzyme or acid to a dextrose equivalent (DE) of about 1 to about 5. The preferred enzyme for liquefaction is bacterial alpha amylase. Next, the selected CGT is added to the gelatinized and liquefied slurry and the pH, temperature and time of the treatment are adjusted depending on the selected enzyme. Generally, the pH is from about 4.5 to about 8.5, the temperature ranges from ambient to about 75° C. and the length of the reaction runs from about ten hours to seven days. The amount of beta cyclodextrin provided will vary depending on the treatment conditions and enzyme selected. Beta cyclodextrin is removed from the raw digest in a conventional manner, such as by crystallization, precipitation or filtration.

In order to produce predominantly beta cyclodextrin, the reaction between CGT and the gelatinized and liquefied starch slurry can be conducted in the presence of a solvent. Such solvents substantially increase the yield of beta cyclodextrin by promoting precipitation of beta cyclodextrin, thereby shifting the equilibrium in favor of continued production of cyclodextrin. Typical solvents include toluene and p-xylene. Such solvents are also referred to as complexants or cyclodextrin complexants because they form complexes with the cyclodextrin and the cyclodextrin precipitates as a complex of cyclodextrin and the complexant. Typically, the solvent is separated from the beta cyclodextrin by boiling an aqueous solution of the complexed beta cyclodextrin. The solvent is distilled and the cyclodextrin is left behind. The cyclodextrin is then recovered from this solution in a conventional manner such as by precipitation, crystallization or filtration.

Separation and purification of non-branched beta cyclodextrin from a solution containing beta cyclodextrin is extremely difficult. One known method for the separation and purification of branched beta cyclodextrin from non-branched beta cyclodextrin is a chromatographic method, see U.S. Pat. No. 5,007,967 issued Apr. 16, 1991.

Another known method is taught in U.S. Pat. No. 4,840,679 issued Jun. 20, 1989. In the '679 patent a beta cyclodextrin complexant is used to separate the branched from the non-branched beta cyclodextrin. However, such a process requires the further processing of the complexed non-branched beta cyclodextrin to separate the complexant from the non-branched cyclodextrin. There is a need for a simple, inexpensive method for purifying non-branched beta cyclodextrin to remove the branched cyclodextrin.

Crystallization is a known technique for industrial purification of materials. Crystallization is, in essence, the precipitation of solid materials from solution. Often, evaporation is used in combination with crystallization to purify materials.

A problem with crystallization is that not all materials form pure crystals. In certain situations, it is known that mixed crystals are formed.

A method for purifying non-branched beta cyclodextrin has now been discovered. Broadly, the purification process of the present invention comprises forming a first or starting aqueous solution containing beta cyclodextrin; forming a first precipitate and a first liquor from the first solution by crystallization; recovering the first precipitate from said first solution; forming a second aqueous solution with the first precipitate; forming a second precipitate and a second liquor from said second solution by crystallization; recovering the second precipitate; and, finally, recovering non-branched beta cyclodextrin from said second precipitate.

Preferably, in order to increase the purity of the non-branched beta cyclodextrin, instead of recovering non-branched beta cyclodextrin from the second precipitate, a third aqueous solution is formed from the second precipitate, and a third crystallization step is performed on the third solution to form a third precipitate and a third liquor; the third precipitate is recovered and, finally, non-branched beta cyclodextrin is recovered from this third precipitate.

The crystallization step of the present invention is performed without the addition of a complexant or solvent. It is noted that there may be some residual solvent which had been used either in the manufacture or recovery of the cyclodextrin from the raw digest of starch or starch hydrolysate with CGT. This residual solvent is also eliminated from the non-branched beta cyclodextrin by the purification process of the present invention. Furthermore, certain acyclic dextrins also appear with the cyclodextrin recovered directly from the raw digest. These acyclic dextrins are also considered to be an impurity and are eliminated by the purification process of the present invention.

Figure 2:
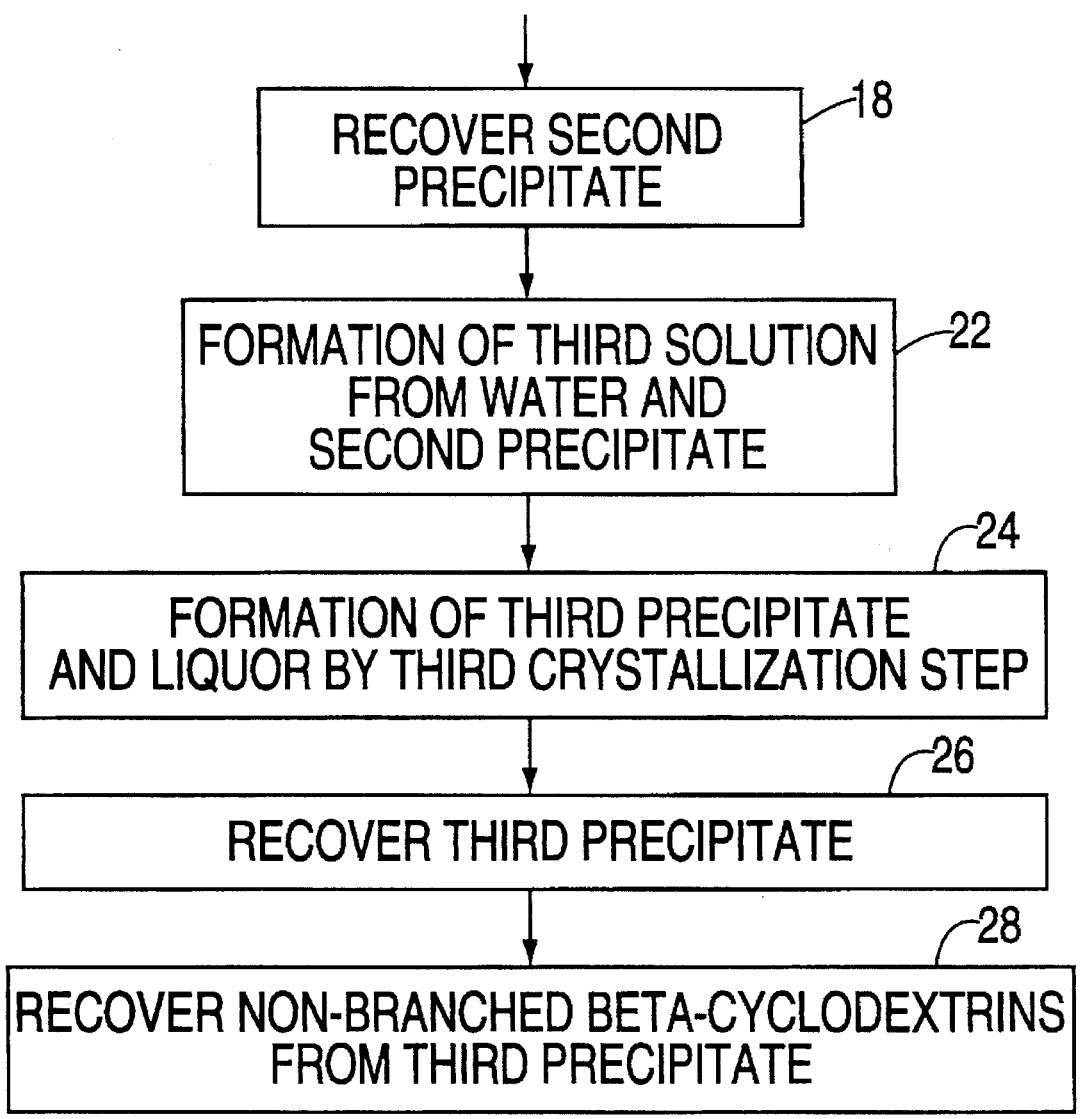

These and other aspects of the present invention may be more fully understood by reference to the accompanying drawings wherein:

FIG. 1 illustrates a broad embodiment of the present invention with respect to non-branched beta cyclodextrin; and FIG. 2 illustrates the additional step of forming a third solution and third precipitate in accordance with the process of the present invention.

As shown in FIG. 1, an aqueous starting solution or first solution is formed, step 8, from beta cyclodextrin which had been recovered from a raw digest, the raw digest having been formed in a conventional manner by the treatment of a starch slurry with a CGT enzyme at the appropriate pH, temperature and length of time for the specific CGT enzyme, and subsequently treated to remove beta cyclodextrin in a crystallization or filtration operation in a conventional manner. Beta cyclodextrin recovered from the raw digest typically has about 85% to about 90% by weight non-branched beta cyclodextrin; about 2% to about 4% by weight branched beta cyclodextrin; and about 6% to about 13% by weight acyclic material.

The starting or first solution in accordance with the present invention comprises water and beta cyclodextrin recovered directly from the raw digest, and has a solids content of about 24% to about 40% by weight, and more preferably, about 25% to about 30% by weight. Heating and mixing in a conventional manner using conventional equipment is used to form the first solution.

Where the beta cyclodextrin has been recovered from the raw digest in the form of a complexed beta cyclodextrin, i.e. a solvent had been used, the formation of the first solution, step 8, entails distillation of the first solution for a sufficient period of time to cause the solvent to evaporate from the solution prior to the first crystallization step. Distillation is done in a conventional manner using conventional equipment. Sometimes, this distillation process will not remove all of the solvent and trace amounts of the solvent remain with the cyclodextrin. The subsequent crystallization step of the present invention eliminates these trace amounts of solvent.

Using this aqueous starting solution a first precipitate and a first liquor are formed by a first crystallization step 10. The first crystallization step 10 is conducted by cooling the first solution down to below about 20° C. and then maintaining the first solution at about 4° C. to about 26° C. for a period of time. Typically, the starting or first solution is at a temperature of about 95° C. and is then cooled to about 20° C.; however, the exact temperature of the starting solution is not critical so long as all of the solid material used to form the first solution is in the solution.

When cooled, the first or starting solution is allowed to stand for a period of about 1 to about 7 days in order for the first precipitate to form. It will be appreciated by those of skill in the art that the first precipitate does not form instantaneously but occurs over a period of time. It has been found that, after a period of about 3 days, all or the majority of the first precipitate has formed. Most preferred is that the time period for forming the precipitate be about 2 days or more.

The equipment used in the first crystallization step can be any conventional crystallization equipment such as a tank crystallizer, an agitated batch crystallizer or a Swenson-Walker crystallizer; preferably, a tank crystallizer is employed for the present invention which is equipped with cooling means such as a cooling gasket that runs around the exterior of the tank. In the agitated batch and Swenson-Walker crystallizers, agitation should be sufficient to suspend crystallization of cyclodextrin.

It has been found that seeding is not necessary.

Recovery of the first precipitate, step 12, is accomplished in a conventional manner using conventional equipment. Filtration or centrifugation can be used, filtration being preferred. Such a step produces the first liquor as a by-product.

The formation of the second solution, step 14, is accomplished by mixing water with the first precipitate in a conventional manner using conventional equipment. Preferably, the precipitate is dissolved in water by heating and stirring the precipitate to form a solution of about 2% to about 35% by weight solids and, more preferably, about 25% to about 30% by weight. It has been found that the amount of heat needed to fully dissolve the first precipitate is such that the second solution boils.

Formation of the second precipitate and liquor is accomplished by a second crystallization step 16. The second crystallization step is accomplished in the same manner as the first crystallization step. The second solution is cooled to below about 20° C. and maintained at a temperature of from about 4° C. to about 26° C. and, more preferably, about 15° C. to about 20° C. to form the second precipitate. Preferably, the time period for forming the second precipitate is about 2 days or more. Conventional crystallization equipment is used in a conventional manner for the second crystallization step.

The recovery of the second precipitate, step 18, from the second solution is accomplished in a conventional manner using conventional equipment such as by centrifugation or filtration. Preferably, the second precipitate is filtered out. Non-branched beta cyclodextrin is then recovered, step 20, from the second precipitate.

If a higher purity of non-branched beta cyclodextrin is preferred, then, prior to recovering non-branched beta cyclodextrin from the second precipitate, a third aqueous solution is formed, step 22, from the second precipitate by mixing the second precipitate with water, as shown in FIG. 2. Next, a third precipitate and a third liquor are formed using a third crystallization step 24. The third precipitate is then recovered, step 26, and non-branched beta cyclodextrin is recovered from the third precipitate, step 28.

The third solution is formed from the second precipitate and water to comprise a solution of about 2% to about 35% by weight solids and, more preferably, about 25% to about 30% by weight. Heating and mixing are used as necessary to form this third solution.

The third crystallization step used to form the third precipitate and third liquor from the third solution is accomplished in the same manner as with the second crystallization step. The third solution is prepared by heating and then cooling the solution to below about 20° C. The temperature of the third solution is maintained during the formation of the third precipitate and liquor at about 4° C. to about 26° C. and, more preferably, about 15° C. to about 20° C. Preferably, the time period for forming the third precipitate is about 2 days or more. The third crystallization step of the third solution is accomplished in a conventional manner using conventional equipment.

The recovering of the third precipitate from the third solution is accomplished in a conventional manner using conventional equipment such as by centrifugation or filtration.

These and other aspects of the present invention may be more fully understood from the following examples.

EXAMPLE 1

A raw digest containing 250 grams of carbohydrate, at 30% solids, was cooled from 95° C. to 20° C. over a period of 24 hours, thereby obtaining cyclodextrin directly from a raw digest. The solution was then filtered on an 18.5 cm paper pad in a Buchner funnel under vacuum. About 90 grams of cyclodextrin were obtained after drying in an oven at 100° C. The analysis conducted on this material is shown in Table 1 below. This analysis can be done on an HPLC column in a conventional manner.

TABLE 1

| Component | Percent by Weight Solids | Total Grams |
|---|---|---|
| Acyclic components | 0.66 | 0.594 |
| Non-branched beta cyclodextrin | 98.97 | 89.07 |
| Branched beta cyclodextrin | 0.37 | 0.333 |

The collected filter cake was then added to 450 ml of distilled water and stirred with a magnetic bar for about 30 minutes and heated to 95° C. to form a first solution. This first solution was then cooled to 20° C. and allowed to stand at 20° C. for 16 hours. The solid precipitate was removed by filtration and the filter cake was oven-dried. This is labelled Precipitate I in Table 2 below. Then, a second solution was formed from Precipitate I in the same manner that the first solution was formed. A second precipitate was formed in the same manner as the first precipitate. This second precipitate is labelled Precipitate II in Table 2 below.

TABLE 2

| | Precipitate I | | Precipitate II | |
|---|---|---|---|---|
| Component | % | Grams | % | Grams |
| Acyclic | 0.11 | 0.0946 | 0 | 0 |
| Total branched beta cyclodextrin | 0.15 | 0.129 | 0 | 0 |
| Total non-branched beta cyclodextrin | 99.74 | 85.78 | 100 | 85 |
| Total solids | 100 | 86 | 100 | 85 |

As can be seen from Table 2 above, the two step crystallization process of the present invention successfully removed 100% of the impurities associated with the non-branched beta cyclodextrin.

It will be understood that the preferred embodiments of the present invention herein chosen for the purpose of illustration are intended to cover all changes and modifications of the preferred embodiments of the invention which do not constitute a departure from the spirit and scope of the invention.

What is claimed is:

1. A process for purifying non-branched beta cyclodextrin comprising the steps of:
   (a) forming a first precipitate and a first liquor from a first solution in a first crystallization step without the addition of a complexant;
   (b) recovering said first precipitate;
   (c) forming a second solution by mixing water with said first precipitate;
   (d) forming a second precipitate and a second liquor from said second solution in a second crystallization step without the addition of a complexant;
   (e) recovering said second precipitate; and
   (f) recovering a purified non-branched beta cyclodextrin from said second precipitate.

2. The process of claim 1 wherein the first crystallization step is conducted by cooling the first solution to a temperature below about 20° C. and maintaining the temperature of the first solution at about 4° C. to about 26° C. for a period of about three days or more.

3. The process of claim 1 wherein the first and second crystallization steps are both conducted by cooling the first and second solutions to a temperature of below about 20° C. and maintaining the temperature of the first and second solutions at about 4° to about 26° C. for a period of about 16 hours or more.

4. The process of claim 1 wherein the recovery step in both steps (b) and (e) is conducted by filtration.

5. A process for purifying non-branched beta cyclodextrin comprising the steps of:
   (a) forming a first precipitate and a first liquor from a first solution in a first crystallization step without the addition of a complexant;
   (b) recovering said first precipitate;
   (c) forming a second solution by mixing water with said first precipitate;
   (d) forming a second precipitate and a second liquor from the second solution by a second crystallization step without the addition of a complexant;
   (e) recovering said second precipitate;
   (f) forming a third solution from said second precipitate;
   (g) forming a third precipitate and a third liquor from said third solution by a third crystallization step without the addition of a complexant;
   (h) recovering said third precipitate; and
   (i) recovering a purified non-branched beta cyclodextrin from said third precipitate.

6. The process of claim 5 wherein the first, second and third crystallization steps are conducted by cooling the first, second and third solutions to a temperature of below about 20° C. and maintaining the temperature of the first, second and third solutions at about 4° to about 26° C. for a period of about 16 hours or more.

7. The process of claim 5 wherein the recovery step in each of steps (b), (e) and (h) is conducted by filtration.

* * * * *